(12) United States Patent
Erneta et al.

(10) Patent No.: US 7,964,211 B2
(45) Date of Patent: Jun. 21, 2011

(54) SEMI-CRYSTALLINE ABSORBABLE MICROSPHERES

(75) Inventors: Modesto Erneta, Princeton Junction, NJ (US); Zhangwen Wu, New Hope, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 12/793,217

(22) Filed: Jun. 3, 2010

(65) Prior Publication Data

US 2010/0240859 A1    Sep. 23, 2010

Related U.S. Application Data

(62) Division of application No. 11/472,777, filed on Jun. 22, 2006.

(51) Int. Cl.
*A61F 2/00* (2006.01)
*C08G 63/82* (2006.01)

(52) U.S. Cl. ........................ 424/426; 528/355

(58) Field of Classification Search ........................ None
See application file for complete search history.

(56) References Cited

U.S. PATENT DOCUMENTS

| | | | |
|---|---|---|---|
| 5,000,886 A * | 3/1991 | Lawter et al. | 264/4.3 |
| 5,236,355 A | 8/1993 | Brizzolara et al. | |
| 6,682,348 B2 | 1/2004 | Lawter et al. | |
| 6,716,251 B1 | 4/2004 | Asius et al. | |
| 2005/0287180 A1 | 12/2005 | Chen | |

FOREIGN PATENT DOCUMENTS

| EP | 0711548 | * 10/1995 |
|---|---|---|
| EP | 0 711 548 A | 5/1996 |

OTHER PUBLICATIONS

Database WPI Week 200430 Derwent Publications Ltd., London, GB 2004-325757 XP002458304 & KR 2003 0077386 A (Gurian Inc.) Oct. 1, 2003.
Tipton, A.J. et al., "Synthetic Biodegradable Polymers as Medical Devices", Medical Plastics and Biomaterials (1998) 3.

* cited by examiner

*Primary Examiner* — Tracy Vivlemore
*Assistant Examiner* — Thurman Wheeler
(74) *Attorney, Agent, or Firm* — E. Richard Skula

(57) ABSTRACT

The present invention is directed to absorbable microspheres comprising a copolymer formed from greater than 88 to about 99 mole percent ε-caprolactone or p-dioxanone, and about 1 to less than 12 mole percent of a different second monomer selected from the group consisting of glycolide, p-dioxanone, trimethylene carbonate and the lactides and combinations thereof, said microspheres having a particle size ranging from about 5 to 2,000 microns. Also described herein are a method for making such microspheres and formulations comprising such absorbable microspheres.

3 Claims, 3 Drawing Sheets

SEMI-CRYSTALLINE ABSORBABLE MICROSPHERES

CROSS REFERENCE TO RELATED APPLICATIONS

This is a divisional application of pending U.S. Ser. No. 11/472,777 filed Jun. 22, 2006.

FIELD OF THE INVENTION

The present invention is directed to semi-crystalline absorbable microspheres that may be used as fillers, a method for making such microspheres and formulations comprising such absorbable microspheres.

BACKGROUND

Fillers can be used in soft tissue augmentation to aesthetically reduce the effects of aging and other soft tissue defects. For example, it is desirable for a filler that is to be used intradermally to be absorbable and soft to the touch. In this case, the filler should not be palpable under the skin either initially upon application or over time. Absorbable polymers that are known to be soft to the touch are those having low glass transition temperatures, including but not limited to ε-caprolactone and p-dioxanone, and copolymers thereof.

A filler is ideally easy to use and produces reproducible and long-lasting results. For example, it may be desirable for the filler to be comprised of microspheres that can pass through a small needle for injection subcutaneously or intradermally, without aggregating or agglomerating under pressure, thereby avoiding clogging of a delivery device such as a needle. Further, if microspheres are utilized, it is desirable for the microspheres to retain their distinct spherical shape without aggregating or agglomerating (hereinafter referred to as "dimensional stability"), upon manufacture, storage and physical transport. Finally, in some situations it may be desirable for these microspheres to retain their distinct spherical shape after implantation, to avoid agglomeration of the microspheres subcutaneously or interdermally, which would produce an unnatural appearance in the skin.

U.S. Pat. No. 6,716,251 describes absorbable microspheres or microparticles suspended in a gel, where the microspheres or microparticles may be polycaprolactones, polylactides, polyglycolides and their copolymers. Although this reference suggests the use of copolymers of polycaprolactones, polylactides, and polyglycolides, preferred polymers are poly-L-lactic acid, poly-D-lactic acid, or a mixture thereof, having a molecular mass ranging from between 70,000 and 175,000 Dalton, and preferably between 120,000 and 170,000 Dalton.

It is possible to achieve the aforementioned combination of properties, i.e., "softness" and dimensional stability, for example, by utilizing copolymers to make microspheres having a low glass transition temperature and sufficient crystallinity to maintain their dimensional stability. Although it is believed that the polylactide microspheres exemplified in U.S. Pat. No. 6,716,251 would have sufficient crystallinity to be dimensionally stable since poly-L-lactides and poly-D-lactides are known to be highly crystalline, one would expect the microspheres to be hard and palpable under the skin, if injected subcutaneously or intradermally, since the glass transition temperature of poly-L-lactide and poly-D-lactide range from 56-65° C.

Therefore, it is desirable to achieve the aforementioned combination of properties of softness and dimensional stability, for example, by utilizing copolymers of ε-caprolactone or p-dioxanone to make microspheres having sufficient crystallinity to maintain their distinct spherical shape during manufacture, storage, transportation and use. Additionally, it is desirable to utilize copolymers of ε-caprolactone or p-dioxanone of specific molecular weights to make microspheres that can be absorbed in the human body within 6 to 24 months after implantation.

More specifically, it is desirable to utilize absorbable copolymers of ε-caprolactone or p-dioxanone that are semi-crystalline in nature, to make microspheres that may be used, for example, in plastic surgery applications and that retain their distinct spherical shape upon manufacture, storage, and physical transportation.

SUMMARY OF THE INVENTION

The present invention is directed to absorbable microspheres comprising a copolymer formed from greater than 88 to about 99 mole percent ε-caprolactone or p-dioxanone, and about 1 to less than 12 mole percent of a different second monomer selected from the group consisting of glycolide, p-dioxanone, trimethylene carbonate and the lactides (L-lactide, D-lactide and meso-lactide) and combinations thereof, said microspheres having a particle size ranging from about 5 to 2,000 microns. Also described herein are a method for making such microspheres and formulations comprising such absorbable microspheres.

DETAILED DESCRIPTION

Figure 1:
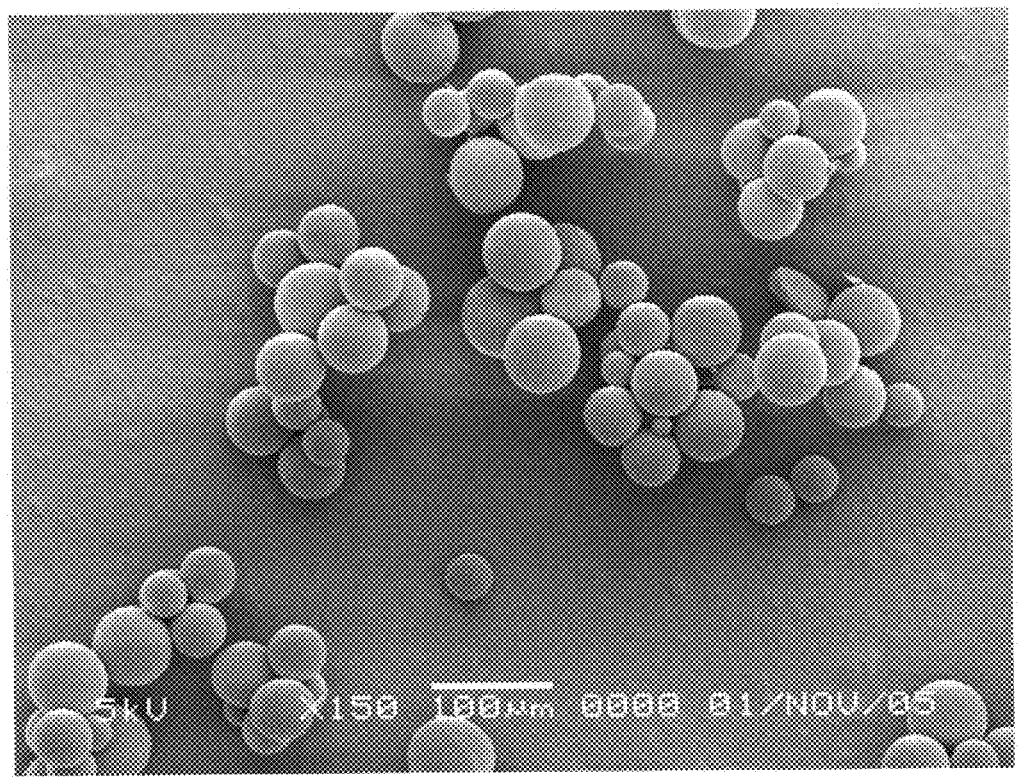
FIG. 1 is a SEM picture of the microspheres made in Example 2 having a crystallinity of 40.1% and a distinct spherical shape.

Described herein are copolymers of ε-caprolactone or p-dioxanone, and at least a different second monomer selected from the group consisting of glycolide, p-dioxanone, trimethylene carbonate and the lactides, that are absorbable within 6 to 24 months and that may be used to make microspheres having a particle size ranging from about 5 to 2,000 microns, and preferably from about 30 to 75 microns. The microspheres described herein are capable of retaining their distinct spherical shape during manufacture, storage, and physical transportation.

The amount of ε-caprolactone or p-dioxanone present in the copolymer described herein ranges from greater than 88 to about 99 mol %, and preferably from about 90 to 97%. The amount of the different second monomer ranges from about 1 to less than 12 mol %, and preferably from about 3 to 10 mol %. Optionally, the copolymer described herein may contain the second monomer in an amount as low as 0.5 to 0.99 mol %, for example, when a ε-caprolactone is polymerized in the presence of a glycolic acid initiator at a ratio of monomer:initiator of 30:1 to 100:1, yielding a polycaprolatone polymer chain having glycolic acid residues incorporated therein. Preferably, the total residual monomer (defined as the total amount of unreacted monomer present in the copolymer) in the copolymer is no greater than about 0.5 weight percent of the microspheres.

In order to achieve absorption of the copolymers described herein by the human body within 6 to 24 months, it is desirable that the copolymer is a semi-crystalline material, having a degree of crystallinity ranging from about 10 to less than 65%, and preferably from about 30 to 45%. Further, the copolymer may be a randomized copolymer, a block copolymer or a segmented block copolymer, having a molecular weight ranging from about 1,000 to about 50,000 daltons, preferably from about 5,000 to 30,000 daltons, and most preferably from about 15,000 to 23,000 daltons.

The microspheres described herein may be made by coacervation, for example as described in U.S. Pat. No. 5,000,886, solvent evaporation, and droplet extrusion with a spinning disk. Other methods of manufacture that may be utilized for formation of microspheres include but are not limited to spray coating, pan-coating, spray-drying, phase separation, emulsion polymerization, and interfacial polymerization.

More specifically, the absorbable microspheres described herein may be prepared from a copolymer formed from about 90 to 97 mole percent ε-caprolactone and about 3 to 10 mole percent of glycolide, said copolymer having a molecular weight of between about 15,000 to 23,000 Daltons, by (a) forming an emulsion of the copolymer, a solvent such as methylene chloride, chloroform, trichloroethylene, and similar solvents with solubility parameters in the range of those described herein ethyl acetate, acetonitrile, tetrahydrofuran, dimethyl sulfoxide and a non-solvent, for example silicone oils such as polydimethylsiloxane, cyclic polydimethylsiloxanes, mineral oils, vegetable oils, wherein the copolymer-solvent forms a microspherical phase and the non-solvent polydimethylsiloxane forms a continuous phase; (b) extracting the microspherical phase using an excess of a volatile silicone fluid such as octamethylcyclotetrasiloxane or decamethylcyclopentasiloxane at a temperature of about 0 to 15° C., and more preferably about 6 to 8° C. when decamethylcyclopentasiloxane is utilized as the volatile solvent and (c) recovering the microspheres by filtration, and drying.

The microspheres described herein may be incorporated into a formulation that is suitable for delivery into the human body via, for example, a syringe. In particular, the formulation may comprise the microspheres suspended in a suspending medium such as a gel. As an example, the formulation may comprise the microspheres, water and a gelling agent approved for use in injections, such as cellulose derivatives, including but not limited to carboxymethylcellulose (CMC), at a concentration by mass ranging from about 0.1 to 7.5%, and preferably from about 0.1 to 5.0%, or hyaluronic acid at a concentration of up to 2% by weight. Additional gelling agents include but are not limited to hydroxypropyl-methylcellulose (HPMC), which is commonly used in intraocular injection during cataract operations; lactic acid esters, caproic acid esters and the like.

Optionally, the formulation may comprise a surfactant, including but not limited to polyoxyethylene sorbitan monooleate (marketed under the brandname Tween 80), Span 20 or pluronic acid, in order to improve the homogeneity of the formulation or gel.

The formulation may be packaged in ready-for-use pre-filled sterile syringes, or in vials. Alternatively, the formulation may be packaged in a vial as freeze-dried product accompanied by a separate ampuole of sterile fluid (i.e., water for injection) that may be combined prior to use; or in a two-compartment pre-filled syringe, one containing the freeze-dried formulation, the other containing water, saline or intravenous solutions or other organic carriers.

While the following examples demonstrate certain embodiments of the invention, they are not to be interpreted as limiting the scope of the invention, but rather as contributing to a complete description of the invention.

Example 1

Synthesis of an ε-Caprolactone/Glycolide Copolymer at a 94:6 (mol/mol) Composition. (94/6 Cap/Gly)

Into an air-tight reactor provided with stirrer and jacket with heating medium is charged 4,695 grams (41.13 moles) of ε-caprolactone, 305 grams (2.627 moles) of glycolide, 110.94 grams (1.459 moles) of glycolic acid, and 5.3 mL of a 0.33 molar solution of stannous octoate in toluene. The reactor is put under vacuum, and the vacuum is broken with nitrogen. The vacuum and nitrogen vacuum breaking step are repeated two more times. The heating medium temperature is raised to 185° C., and when the batch temperature reaches 180° C. the polymerization reaction is allowed to proceed for 6 additional hours. The reactor is then put under vacuum for one hour to remove unreacted monomer. The molten polymer is dropped from the reactor and collected as polymer blocks. After cooling to room temperature, the polymer is further cooled under liquid nitrogen, before it is ground into powder with a polymer grinder. The molar composition of the polymer by $^1$H NMR analysis is:

| | |
|---|---|
| Polycaprolactone | 93.6% |
| PGA | 6.2% |
| Glycolide | 0.0% |
| ε-caprolactone | 0.3% |

The inherent viscosity in hexafluoroisopropanol at a solution concentration of 0.1 g/dL is 0.38 dL/g. The weight average molecular weight (Mw) is 7,540 Daltons.

Formation of Microspheres from the 94/6 ε-Caprolactone/Glycolide Copolymer:

Microspheres are formed in a 2-liter resin flask provided with stirrer, nitrogen inlet, condenser and cold trap by the following solvent evaporation process. The flask is charged with 1,650 grams of a 3% w/w polyvinyl alcohol water solution. Stirrer rotation is set at about 246 RPM. A 7.5% w/w solution of the 94/6 ε-caprolactone/glycolide copolymer (cap/gly copolymer) in methylene chloride (277.8 grams of solution) is substantially uniformly added over a period of about 13 minutes into the side of the vortex, forming an oil in water emulsion. Methylene choride is evaporated by passing nitrogen over the surface of the stirred solution for about 14 hours. The agitation is stopped and the formed microspheres are allowed to settle at the bottom of the flask and the supernatant liquid is removed. The microspheres are repeatedly washed with deionized water, allowing time for settling of the microspheres at the bottom of is the flask before removing the supernatant liquid. The microspheres are wet-screened from the water slurry using two stacked stainless steel screens (screen sizes 38 microns and 75 microns), and collecting the fraction between 38 and 75 microns. The microspheres are then vacuum dried at room temperature until removal of water is accomplished. A total of 14.8 grams of microspheres is collected, giving a yield of 71%.

The microspheres showed a crystallinity of 38.7% as measured by x-ray diffraction and Scanning Electron Microscopy (SEM) pictures showed microspheres having distinct spherical shape. The microspheres are sterilized in closed vials by gamma radiation at 25 kGy and are easily re-dispersed in sterile sodium carboxymethylcellulose, water solutions, or saline water solutions, as well as in a sodium hyaluronate water, or saline water solutions, having viscosities in the range of about 5 to about 50 centipoises.

Example 2

Synthesis of an ε-Caprolactone/Glycolide Copolymer at a 97:3 (mol/mol) Composition. (97/3 Cap/Gly)

Into an air-tight reactor provided with stirrer and jacket with heating medium is charged 4,847.5 grams (42.47 moles) of ε-caprolactone, 152.5 grams (1.3138 moles) of glycolide, 51.227 grams (0.673 moles) of glycolic acid, and 5.3 mL of a 0.33 molar solution of stannous octoate in toluene. The reactor is put under vacuum, and the vacuum is broken with nitrogen. The vacuum and nitrogen vacuum breaking step are repeated two more times. The heating medium temperature is raised to 185° C. and when the batch temperature reaches 180° C. the polymerization reaction is allowed to proceed for 6 additional hours. The reactor is then put under vacuum for one hour to remove unreacted monomer. The molten polymer is dropped from the reactor and collected as polymer blocks. After cooling to room temperature, the polymer is further cooled under liquid nitrogen, before it is ground into powder with a polymer grinder. The molar composition of the polymer by $^1$H NMR analysis is:

| | |
|---|---|
| polycaprolactone | 96.9% |
| PGA | 3.1% |
| glycolide | 0.0% |
| ε-caprolactone | 0.0% |

The weight average molecular weight (Mw) is 15,100 Daltons.
Formation of Microspheres from the 97/3 ε-Caprolactone/Glycolide Copolymer:

Microspheres are formed in a 2-liter resin flask provided with stirrer, nitrogen inlet, condenser and cold trap by the following solvent evaporation process: The flask is charged with 1,412 grams of a 3% w/w polyvinyl alcohol water solution. Stirrer rotation is set at about 246 RPM. A 7.5% w/w solution of the 97/3 cap/gly polymer in methylene chloride (231.2 grams of solution) is substantially uniformly added over a period of about 16 minutes into the side of the vortex, forming an oil in water emulsion. Methylene choride is evaporated by passing nitrogen over the stirred surface of the solution for about 14 hours. The agitation is stopped and the formed microspheres are allowed to settle at the bottom of the flask and the supernatant liquid is removed. The microspheres are repeatedly washed with deionized water allowing time for settling of the microspheres at the bottom of the flask before removing the supernatant liquid. The microspheres are wet-screened from the water slurry using two stacked stainless steel screens (screen sizes 38 microns and 75 microns) and the fraction between 38 and 75 microns is collected. The microspheres are then vacuum dried at room temperature until removal of water is accomplished.

The microspheres show a crystallinity of 40.1% and SEM pictures of the microspheres after wet-screening and drying in FIG. 1, show microspheres having distinct spherical shape. The microspheres are sterilized in closed vials by gamma radiation at 25 kGy, at a dose rate of 14.32 kGy/hr. and are easily re-dispersed in sterile sodium carboxymethylcellulose, water solutions, or saline water solutions, as well as in a sodium hyaluronate water, or saline water solutions having viscosities in the range of about 5 to about 50 centipoises.

Example 3

Synthesis of a Polycaprolactone Polymer Initiated with Glycolic Acid at a Monomer to Initiator Ratio of 30/1

Into an air-tight reactor provided with stirrer and jacket with heating medium is charged 5,000 grams (43.8 moles) of ε-caprolactone, 111.05 grams (1.46 moles) of glycolic acid, and 5.3 mL of a 0.33 molar solution of stannous octoate in toluene. The reactor is put under vacuum, and the vacuum is broken with nitrogen. The vacuum and nitrogen vacuum breaking step are repeated two more times. The heating medium temperature is raised to 185° C. and when the batch temperature reaches 180° C. the polymerization reaction is allowed to proceed for 6 additional hours. The reactor is then put under vacuum for one hour to remove unreacted monomer. The molten polymer is dropped from the reactor and collected as polymer blocks. After cooling to room temperature, the polymer is further cooled under liquid nitrogen, before it is ground into powder with a polymer grinder. The molar composition of the polymer by $^1$H NMR analysis is:

| | |
|---|---|
| polycaprolactone | 98.7% |
| PGA | 1.3% |
| ε-caprolactone | 0.% |

The weight average molecular weight is 6,600 Daltons.
Formation of Microspheres from the Polycaprolactone Polymer Initiated with Glycolic Acid at a Monomer to Initiator Ratio of 30/1:

Microspheres are formed in a 2 liter resin flask provided with stirrer, nitrogen inlet, condenser and cold trap by the following solvent evaporation process: The flask is charged with 1,500 grams of a 3% w/w polyvinyl alcohol water solution. Stirrer rotation is set at about 240 RPM. A 7.5% w/w solution of the glycolic acid initiated polycaprolactone polymer in methylene chloride (270 grams of solution) is substantially uniformly added over a period of about 19 minutes into the side of the vortex, forming an oil in water emulsion. Methylene choride is evaporated by passing nitrogen over the surface of the solution for about 16 hours. The agitation is stopped and the formed microspheres are allowed to settle at the bottom of the flask and the supernatant liquid is removed. The microspheres are repeatedly washed with deionized water, allowing time for settling of the microspheres at the bottom of the flask before removing the supernatant liquid. The microspheres are wet-screened from the water slurry using two stacked stainless steel screens (screen sizes 38 microns and 75 microns), and collecting the fraction between 38 and 75 microns. The microspheres are then vacuum dried at room temperature until removal of water is accomplished, and subsequently are dried at 40° C. for 16 hours. A total of 7.28 grams of microspheres is collected.

The microspheres are sterilized in closed vials by gamma radiation at 25 kGy and are easily re-dispersed in sterile sodium carboxymethylcellulose, water solutions, or saline water solutions, as well as in a sodium hyaluronate water, or saline water solutions, having viscosities in the range of about 5 to about 50 centipoises.

Example 4

Synthesis of a Polycaprolactone Polymer Initiated with Glycolic Acid at a Monomer to Initiator Ratio of 100/1

Into an air-tight reactor provided with stirrer and jacket with heating medium is charged 5,000 grams (43.8 moles) of ε-caprolactone, 33.31 grams (0.438 moles) of glycolic acid, and 5.3 m. of a 0.33 molar solution of stannous octoate in toluene. The reactor is put under vacuum, and the vacuum is broken with nitrogen. The vacuum and nitrogen vacuum breaking step are repeated two more times. The heating medium temperature is raised to 185° C. and when the batch temperature reaches 180° C. the polymerization reaction is allowed to proceed for 6 additional hours. The reactor is then put under vacuum for one hour to remove unreacted monomer. The molten polymer is dropped from the reactor and collected as polymer blocks. After cooling to room temperature, the polymer is further cooled under liquid nitrogen, before it is ground into powder with a polymer grinder. The molar composition of the polymer by $^1$H NMR analysis is:

| | |
|---|---|
| polycaprolactone | 99.4% |
| PGA | 0.5% |
| ε-caprolactone | 0.1% |

The weight average molecular weight is 20,200 Daltons.
Formation of Microspheres from the Polycaprolactone Polymer Initiated with Glycolic Acid at a Monomer to Initiator Ratio of 100/1:

Microspheres are formed in a 2-liter resin flask provided with stirrer, nitrogen inlet, condenser and cold trap by the following solvent evaporation process: The flask is charged with 1,500 grams of a 3% w/w polyvinyl alcohol water solution. Stirrer rotation is set at about 240 RPM. A 7.5% w/w solution of the glycolic acid initiated polycaprolactone polymer in methylene chloride (270 grams of solution) is substantially uniformly added over a period of about 12 minutes into the side of the vortex, forming an oil in water emulsion. Methylene choride is evaporated by passing nitrogen over the surface of the solution for about 16 hours. The agitation is stopped and the formed microspheres are allowed to settle at the bottom of the flask and the supernatant liquid is removed. The microspheres are repeatedly washed with deionized water, allowing time for settling of the microspheres at the bottom of the flask before removing the supernatant liquid. The microspheres are wet-screened from the water slurry using two stacked stainless steel screens (screen sizes 38 microns and 75 microns) and collecting the fraction between 38 and 75 microns. The microspheres are then vacuum dried at room temperature until removal of water is accomplished, and subsequently are dried at 40° C. for 16 hours. A total of 7.28 grams of microspheres is collected.

The microspheres are sterilized in closed vials by gamma radiation at 25 kGy and are easily re-dispersed in sterile sodium carboxymethylcellulose, water solutions, or saline water solutions, as well as in a sodium hyaluronate water, or saline water solutions, having viscosities in the range of about 5 to about 50 centipoises.

Comparative Example 5

Synthesis of an ε-Caprolactone/Glycolide Copolymer at a 88:12(mol/mol) Composition. (88/12 Cap/Gly)

Into a 500 ml round bottom flask provided with mechanical stirrer is charged 30.45 grams (0.262 moles) of glycolide, 219.55 grams (1.92 moles) ε-caprolactone, 1.66 grams (0.0218 moles) of glycolic acid, and 0.26 ml. of a 0.33 molar solution of stannous octoate in toluene. The flask is put under is vacuum for one hour. The flask is purged with nitrogen, and it is immersed in a hot oil bath kept at 190° C. for 16 hours, with mixing. At the end of the reaction, the molten polymer is poured into trays, where it cools to room temperature. The polymer is then ground and kept under vacuum at room temperature.

The molar composition of the polymer by $^1$H NMR analysis is:

| | |
|---|---|
| polycaprolactone | 87.5% |
| PGA | 12.4% |
| ε-caprolactone | 0.1% |

Figure 2:
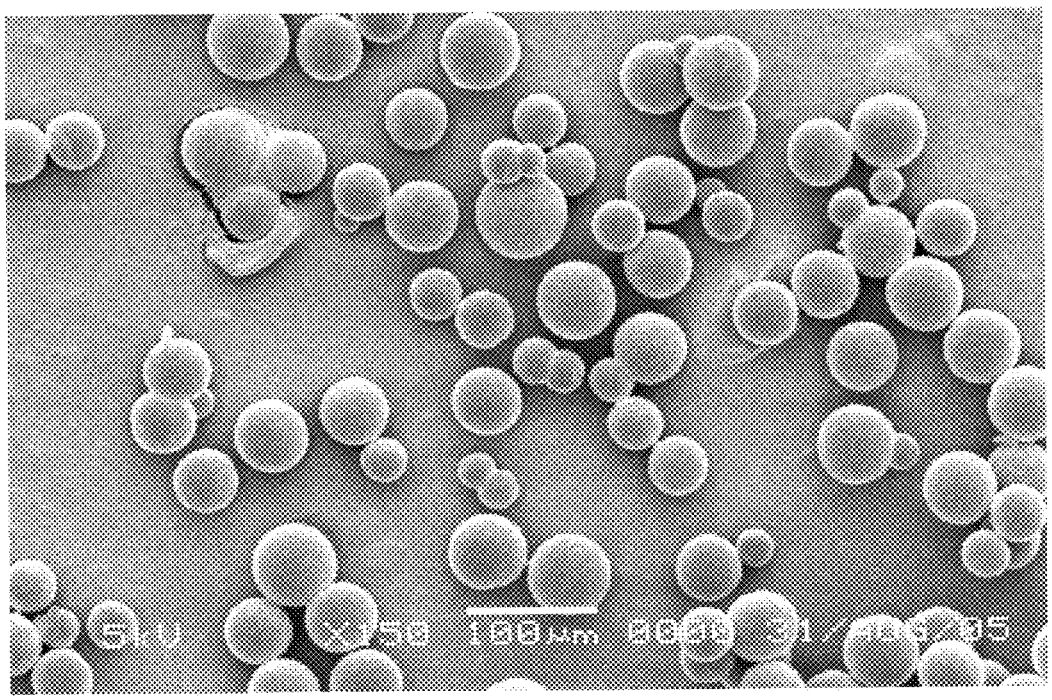
FIG. 2 is a SEM picture of the microspheres made in Comparative Example 5, revealing the formation of some agglomerates.

The weight average molecular weight is 10,300 Daltons
Formation of Microspheres from the 88/12 ε-Caprolactone/Glycolide Copolymer:

Microspheres are formed in a 2-liter resin flask provided with stirrer, nitrogen inlet, condenser and cold trap by the following solvent evaporation process: The flask is charged with 1,625 grams of a 3% w/w polyvinyl alcohol water solution. Stirrer rotation is set at about 241 RPM. A 7.5% w/w solution of the 88/12 cap/gly copolymer in methylene chloride (269.1 grams of solution) is substantially uniformly added over a period of about 15 minutes into the side of the vortex, forming an oil in water emulsion. Methylene chloride is evaporated by passing nitrogen over the surface of the solution for about 16 hours. The agitation is stopped and the formed microspheres are allowed to settle at the bottom of the flask and the supernatant liquid is removed. The microspheres are repeatedly washed with deionized water, allowing time for settling of the microspheres at the bottom of the flask before removing the supernatant liquid. The microspheres are wet-screened from the water slurry using two stacked stainless steel screens (screen sizes 38 microns and 75 microns) and collecting the fraction between 38 and 75 microns. The microspheres are then vacuum dried at room temperature until removal of water is accomplished, and subsequently are dried at 40° C. for 16 hours. The microspheres were examined by SEM under high vacuum. The photographs of the microspheres after wet-screening and drying shown in FIG. 2 reveal formation of some agglomerates, which are not seen at compositional ranges of higher ε-caprolactone content.

Comparative Example 6

Synthesis of an ε-Caprolactone/Glycolide Copolymer at a 85:15(mol/mol) Composition. (85/15 Cap/Gly)

Into a 500 ml round bottom flask provided with mechanical stirrer is charged 38.04 grams (0.328 moles) of glycolide, 211.96 grams (1.86 moles) ε-caprolactone, 5.54 grams (0.072 moles) of glycolic acid, and 0.26 ml. of a 0.33 molar solution of stannous octoate in toluene. The flask is put under vacuum for one hour. The flask is purged with nitrogen, and it is immersed in a hot oil bath kept at 190° C. for 16 hours, with mixing. At the end of the reaction, the molten polymer is poured into trays, where it cools to room temperature. The polymer is then ground and kept under vacuum at room temperature.

The molar composition of the polymer by $^1$H NMR analysis is:

| | |
|---|---|
| polycaprolactone | 84.6% |
| PGA | 14.5% |
| ε-caprolactone | 0.9% |

The weight average molecular weight was Mw=23,500 Daltons

Formation of Microspheres from the 85/15 ε-Caprolactone/Glycolide Copolymer:

An attempt to form microspheres under the same experimental conditions described in Comparative Example 5 failed to produce microspheres, and resulted in the formation of agglomerates.

Example 7

Synthesis of an ε-Caprolactone/Glycolide Copolymer at a 94:6 (mol/mol) Composition. (94/6 Cap/Gly) at a Monomer to Glycolic Acid Molar Ratio of 100/1

Into an air-tight reactor provided with stirrer and jacket with heating medium is charged 4,695 grams (41.13 moles) of ε-caprolactone, 305 grams (2.627 moles) of glycolide, 33.28 grams (0.438 moles) of glycolic acid, and 5.3 mL. of a 0.33 molar solution of stannous octoate in toluene. The reactor is put under vacuum, and the vacuum is broken with nitrogen. The vacuum, and nitrogen vacuum breaking step are repeated two more times. The heating medium temperature is raised to 185° C., and when the batch temperature reaches 180° C. the polymerization reaction is allowed to proceed for 6 additional hours. The reactor is then put under vacuum for one hour to remove unreacted monomer. The molten polymer is dropped from the reactor and collected as polymer blocks. After cooling to room temperature, the polymer is further cooled under liquid nitrogen, before it is ground into powder with a polymer grinder. The molar composition of the polymer by $^1$H NMR analysis is: polycaprolactone 93.9%

| | |
|---|---|
| PGA | 5.5% |
| glycolide | 0.% |
| ε-caprolactone | 0.6% |

The inherent viscosity in hexafluoroisopropanol at a solution concentration of 0.1 g/dL is 0.73 dL/g. The weight average molecular weight is 18,900 Daltons.

Figure 3:
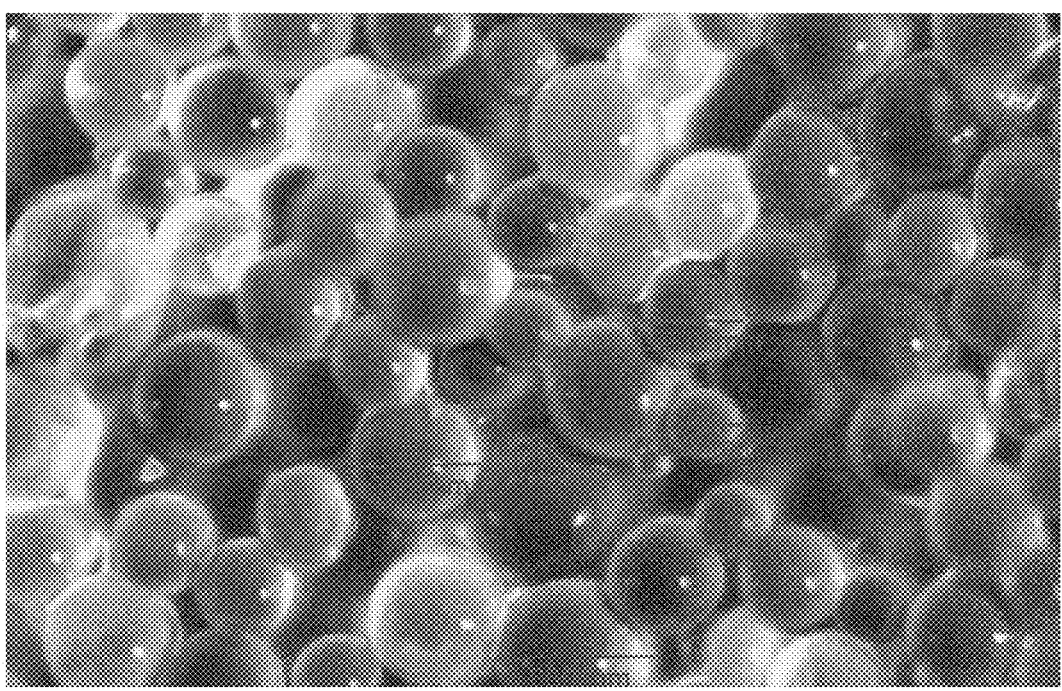
FIG. 3 is a photomicrograph showing the microspheres of Example 7.

Formation of Microspheres from the 94/6 ε-Caprolactone/Glycolide Copolymer with a Monomer to Glycolic Acid Molar Ratio of 100/1 by a Coacervation Method:

Into a 200 mL cylindrical glass container is charged 62.5 grams of a 4.0% w/w solution of 94/6 ε-caprolactone/glycolide copolymer copolymer in methylene chloride. 250 grams of polydimethylsiloxane (360 Medical Fluid, 350 CST, commercially available from Dow Corning) is slowly added to the polymer solution under stirring to form 312.5 grams of emulsion. The polymer solution is broken down into droplets by agitation and dispersed in the polydimethylsiloxane continuous phase to form microspheres. The emulsion is continuously agitated for about 150 minutes. The emulsion was transferred to another glass container containing approximately 3,125 grams of decamethylcyclopentasiloxane (PENTAMERE SILBIONE® D5, commercial available from Rhodia) at a controlled temperature of about 6° C. with stirring to harden the microspheres. The mixture is kept at a temperature of 6° C. with stirring for approximately 120 minutes to achieve full solvent extraction and hardening of the polymeric microspheres. The microspheres are recovered by filtration utilizing a 10 micron stainless steel screen filter. The microspheres are washed on the filter with fresh decamethylcyclopentasiloxane, and they are dried under vacuum. FIG. 3 is a photomicrograph showing particle uniformity.

Comparative Example 8

Microspheres from the 94/6 ε-caprolactone/glycolide copolymer of Example 7 are made by the coacervation method under different conditions.

Into a 200 mL cylindrical glass container is charged 120 grams of a 2.5% w/w solution of 94/6 ε-caprolactone/glycolide copolymer in methylene chloride. Polydimethylsiloxane, 270 grams (360 Medical Fluid, 350 CST, commercially available from Dow Corning), is slowly added to the polymer solution under stirring to form 390 grams of emulsion. The polymer solution is broken down into droplets by agitation and dispersed in the polydimethylsiloxane continuous phase to form microspheres. The emulsion is continuously agitated for about 120 minutes. The emulsion was transferred to another glass container containing approximately 3,108 grams of decamethylcyclopentasiloxane (PENTAMERE SILBIONE® D5, commercial available from Rhodia) at a room temperature of 24° C. to harden the microspheres with stirring. A couple of minutes after the emulation is transferred, the aggregation of the microspheres occurs.

What is claimed is:

1. A method for making absorbable microspheres comprising a copolymer formed from about 88 to 97 mole percent epsilon-caprolactone and about 3 to less than 12 mole percent of glycolide, said copolymer having a crystallinity level ranging from about 30 to 45% and a molecular weight of the copolymer between about 3,000 to 23,000 Daltons; and said microspheres having a distribution of particle sizes from about 30 to 90 microns; comprising the steps of:

(a) forming an emulsion of said copolymer, methylene chloride and a polydimethylsiloxane, wherein the copolymer forms microspheres in a microspherical phase and the polydimethylsiloxane forms a continuous phase;

(b) extracting the microspherical phase using an excess of decamethylcyclopentasiloxane at a temperature of less than 15 degrees C and above the freezing point to decamethycyclopentasiloxane; and (c) recovering the microspheres by filtration wherein the microspheres have a distinct spherical shape.

2. The method of claim 1, wherein said distribution of particle sizes is from about 30 to 50 microns.

3. The method of claim 1, wherein said molecular weight copolymer is between about 15,000 to 23,000 Daltons.

* * * * *